(12) United States Patent
Bortlik et al.

(10) Patent No.: US 8,455,004 B2
(45) Date of Patent: Jun. 4, 2013

(54) PRIMARY COMPOSITION COMPRISING A LIPOPHILIC BIOACTIVE COMPOUND

(75) Inventors: Karlheinz Bortlik, Syens (CH); Francoise Saucy, Blonay (CH); Eliane Duruz, Epalinges (CH); Myriam Richelle, Savigny (CH); Pierre Lambelet, Saint-Legier (CH); Markus Baur, Ulm (DE); Andrea Pfeifer, Saint-Legier (CH)

(73) Assignee: Nestec S.A., Vevey (CH)

( * ) Notice: Subject to any disclaimer, the term of this patent is extended or adjusted under 35 U.S.C. 154(b) by 583 days.

(21) Appl. No.: 12/353,730

(22) Filed: Jan. 14, 2009

(65) Prior Publication Data

US 2009/0123542 A1    May 14, 2009

Related U.S. Application Data

(63) Continuation of application No. 11/004,409, filed on Dec. 3, 2004, now abandoned, which is a continuation-in-part of application No. 10/057,660, filed on Jan. 25, 2002, now abandoned, and a continuation of application No. PCT/EP01/06145, filed on May 29, 2001.

(30) Foreign Application Priority Data

May 30, 2000   (EP) .................................. 00111542

(51) Int. Cl.
*A61K 35/20*   (2006.01)
(52) U.S. Cl.
CPC ..................................... *A61K 35/20* (2013.01)
USPC ............ 424/535; 424/400; 424/439; 424/725

(58) Field of Classification Search
CPC . A23V 2002/02; A23V 2200/324; A61K 35/20
USPC .................................. 424/400, 439, 535, 725
See application file for complete search history.

(56) References Cited

U.S. PATENT DOCUMENTS

| | | | |
|---|---|---|---|
| 4,522,743 A | 6/1985 | Horn et al. | |
| 4,961,934 A * | 10/1990 | Iwasaki et al. | 426/2 |
| 5,235,315 A | 8/1993 | Cherry et al. | |
| 5,601,760 A | 2/1997 | Rosenberg | |
| 5,643,623 A | 7/1997 | Schmitz et al. | |
| 5,706,526 A | 1/1998 | Huang | |
| 5,855,892 A | 1/1999 | Potter et al. | |
| 6,042,815 A * | 3/2000 | Kellner et al. | 424/63 |
| 6,203,805 B1 | 3/2001 | Collins et al. | |

FOREIGN PATENT DOCUMENTS

| | | |
|---|---|---|
| EP | 0 278 284 | 8/1988 |
| EP | 0 986 963 | 3/2000 |
| GB | 1 521 691 | 8/1978 |

* cited by examiner

*Primary Examiner* — Ruth Davis
(74) *Attorney, Agent, or Firm* — K&L Gates LLP

(57) ABSTRACT

The invention relates to a primary composition in which at least one lipophilic bioactive compound is mixed with a whey protein, present in an amount effective to increase the bioavailability of the lipophilic bioactive compound. The invention also relates to an oral composition that contains the primary composition in a foodstuff, in a food supplement, or in a pharmaceutical preparation, and to a cosmetic preparation that contains the primary composition. Methods for increasing the bioavailability of the lipophilic bioactive compound and providing increased photostability and oxidation resistance are also provided.

13 Claims, No Drawings

PRIMARY COMPOSITION COMPRISING A LIPOPHILIC BIOACTIVE COMPOUND

CROSS-REFERENCE TO RELATED APPLICATIONS

This application is a continuation of U.S. Ser. No. 11/004,409, filed Dec. 3, 2004, which is a continuation-in-part of U.S. Ser. No. 10/057,660, filed Jan. 25, 2002, which is a continuation of International application PCT/EP01/06145, filed May 29, 2001, the entire contents of which are expressly incorporated herein by reference thereto.

TECHNICAL FIELD

The present invention relates to a primary composition comprising a lipophilic bioactive compound and to an oral composition comprising the primary composition.

BACKGROUND

Compositions available on the market that include a lipophilic bioactive compound (LBC), namely lycopene, are already known. Lycopene is a natural product which is known to have multiple roles, in particular that of an antioxidant. Lycopene is present in various natural products, in particular tomatoes, melons, guavas and grapefruit.

The composition generally available on the market which comprises lycopene is an oleoresin. The problem with this oleoresin is that it has been found that the lycopene present therein is insufficiently bioavailable. For example, EP 278 284 seeks to improve the color strength and absorption of carotenoids for the purposes of coloring food and animal feeds by dividing the carotenoids into small particles. This is achieved by forming a pulverulent water-dispersible carotenoid formulation through a complex, multi-stage process to convert the carotenoids into a finely divided, pulverulent form, with a particle size of about 191-359 nm (according to the Examples) and an improved coloring strength. The pulverulent formulations is envisaged for a coloring purpose only and does not disclose the use of a whey protein.

While some prior art references have sought to provide LBCs for health-related purposes, the prior art merely relates to providing certain types of LBC or focuses on the way the LBC is delivered, and does not mention increasing the bioavailability of the LBC itself. For instance, U.S. Pat. No. 5,855,892 relates to providing daidzein that is preferably isolated from soy material. U.S. Pat. No. 5,705,526 provides lycopene in a soft-capsulated drug, where the lycopene is provided in mixture with oil such that the fluidity of the contents of the capsule is increased. U.S. Pat. No. 5,643,623 seeks to deliver antioxidant in a food product by embedding the antioxidant within or discrete from other components such as fat, carbohydrate or protein. U.S. Pat. No. 5,601,760 discloses microencapsulating volatile or non-volatile core materials with whey protein-based microencapsulating agents to improve the delivery of the core materials. U.S. Pat. No. 6,203,805 discloses a topical composition comprising a collagen-enhancing effective amount of whey protein and vitamins A, E and C, in which vitamins E and C are present in specific ranges based on their inverse effect in boosting collagen synthesis.

None of the prior art references, however, addresses increasing the bioavailability of LBC and of further preserving LBC activity in an oral product, wherein the LBC is in unencapsulated form. Thus, there is a need for an LBC-containing product in which the LBC is provided with better bioavailability than the products currently on the market through a simple, manufacture-friendly process. Applicants have now surprisingly discovered that the bioavailability of a LBC can be enhanced by associating the LBC with whey protein such that the LBC and the whey protein are provided in a form of a mixture or a matrix. Further, by providing the LBC in an unencapsulated form and in mixture with whey protein, the present invention also seeks to protect and preserve the activity of the LBC. In particular, Applicants have found that the compound's resistance to decomposition by light and oxygen is significantly increased by associating the LBC with whey protein in a mixture or matrix as detailed below.

SUMMARY OF THE INVENTION

The invention relates to a primary composition in which at least one LBC is associated with a whey protein that is present in an amount effective to increase the bioavailability of the LBC. Preferably the LBC and why protein are associated as a mixture or matrix.

The LBC is advantageously obtained, extracted, enriched or purified from a plant, microorganism, yeast or product of animal origin. Where the LBC is obtained from a plant source, the plant may be tomatoes, soya, green tea, green coffee beans, spices, grapes, cocoa, ginger or cereals. Where it is obtained from microorganism, the microorganism may be any type of bacterium that produces a LBC. Where the LBC comes from yeast, the yeast may be a yeast which produces a LBC, and when it is obtained from a product of animal origin, the product of animal origin may be chosen from the group consisting of a liver extract and a milk fraction.

The LBC may be a carotenoid, polyphenol, lipophilic vitamin, flavonoid; isoflavone, curcuminoid, ceramide, proanthocyanidin, terpenoid, sterol, phytosterol, sterol ester, tocotrienol, squalene, or retinoid, alone or as a mixture. The LBC may be a tomato extract, a soybean extract or a mixture thereof.

The primary composition may be in the form of a powder, gel or liquid, and the composition may further comprise at least one of vitamin C or tocopherol. The primary composition may also comprise at least one of an emulsifier, a stabilizer or another additive. The primary composition may advantageously be in an unencapsulated form.

The preferred form of the primary composition is as an oral composition for oral administration, such as in a foodstuff, a food supplement, or a pharmaceutical preparation, or as a cosmetic composition. The foodstuff may be a yogurt, a liquid drink, a chocolate containing product, an ice cream, cereal, coffee or animal food. Where the oral composition is provided as a food supplement, the food supplement may further comprise at least one of a sweetener, a stabilizer, a flavoring or a colorant. A cosmetic preparation comprising the primary composition may additionally comprise a compound active with respect to the skin. A cosmetic or pharmaceutical preparation according to the present invention may be provided in the form of sugar-coated tablets, pills, gelatin capsules, a syrup, a gel or a cream.

In preferred embodiments, the content of the primary composition is between about 0.001 and 100% in an oral composition and between about $10^{-10}$% and 10% in a cosmetic composition.

The primary composition according to the present invention may comprise a LBC in an amount of about 0.05 to 50% by weight of the composition and a whey protein in an amount of about 5 to 90% by weight of the composition, wherein the whey protein and the LBC are present in a weight ratio of about 1:1 to 500:1, and advantageously in a weight ratio of about 1.5:1 to 250:1. In a further advantageous embodiment, the primary composition may comprise at least one LBC of a tomato oleoresin, a soybean extract, or a mixture thereof, and a whey protein in an amount effective to increase the bioavailability of the LBC, wherein the LBC is present in an amount of about 0.05 to 50% by weight of the composition and the whey protein is present in an amount of about 5 to 90% by weight of the composition and wherein the whey protein and LBC are present in a weight ratio of about 1:1 to 500:1. Preferably the LBC. comprises lycopene. Where the primary composition is used in an oral composition, such as in a foodstuff, a food supplement or a pharmaceutical preparation, the The LBC may be a carotenoid, polyphenol, lipophilic vitamin, flavonoid, isoflavone, curcuminoid, ceramide, proanthocyanidin, terpenoid, sterol, phytosterol, sterol ester, tocotrienol, squalene, or retinoid, alone or as a mixture. The LBC may be a tomato extract, a soybean extract or a mixture thereof.

The primary composition may be in the form of a powder, gel or liquid, and the composition may further comprise at least one of vitamin C or tocopherol. The primary composition may also comprise at least one of an emulsifier, a stabilizer or another additive. The primary composition may advantageously be in an unencapsulated form.

The preferred form of the primary composition is as an oral composition for oral administration, such as in a foodstuff, a food supplement, or a pharmaceutical preparation, or as a cosmetic composition. The foodstuff may be a yogurt, a liquid drink, a chocolate containing product, an ice cream, cereal, coffee or animal food. Where the oral composition is provided as a food supplement, the food supplement may further comprise at least one of a sweetener, a stabilizer, a flavoring or a colorant. A cosmetic preparation comprising the primary composition may additionally comprise a compound active with respect to the skin. A cosmetic or pharmaceutical preparation according to the present invention may be provided in the form of sugar-coated tablets, pills, gelatin capsules, a syrup, a gel or a cream.

In preferred embodiments, the content of the primary composition is between about 0.001 and 100% in an oral composition and between about $10^{-10}$% and 10% in a cosmetic composition.

The primary composition according to the present invention may comprise a LBC in an amount of about 0.05 to 50% by weight of the composition and a whey protein in an amount of about 5 to 90% by weight of the composition, wherein the whey protein and the LBC are present in a weight ratio of about 1:1 to 500:1, and advantageously in a weight ratio of about 1.5:1 to 250:1. In a further advantageous embodiment, the primary composition may comprise at least one LBC of a tomato oleoresin, a soybean extract, or a mixture thereof, and a whey protein in an amount effective to increase the bioavailability of the LBC, wherein the LBC is present in an amount of about 0.05 to 50% by weight of the composition and the whey protein is present in an amount of about 5 to 90% by weight of the composition and wherein the whey protein and LBC are present in a weight ratio of about 1:1 to 500:1. Preferably the LBC comprises lycopene. Where the primary composition is used in an oral composition, such as in a foodstuff, a food supplement or a pharmaceutical preparation, the whey protein and lipophilic bioactive compound may be present in a weight ratio of at least about 2:1 to 20:1.

The present invention further comprises a process of preparing the primary composition. The process comprises the step of mixing the whey protein with the lipophilic bioactive compound to produce the primary composition.

In a preferred embodiment the step of mixing is accomplished by dissolving the whey protein in water to produce a first solution; dissolving the lipophilic bioactive compound in a solvent to product a second solution; mixing the first and second solutions; and evaporating the solvent and water to produce the primary composition. The process may further comprise the step of heat-treating the primary composition to produce a gel. The lipophilic bioactive compound may comprise oleoresin comprising between 1 and 40% lycopene.

The present invention also provides methods for increasing bioavailability of a lipophilic bioactive compound to a subject upon administration by associating a whey protein with a lipophilic bioactive compound to form a primary composition and administering the primary composition to the subject, such that increased amounts of the lipophilic bioactive compound are released as compared to lipophilic compositions that do not include whey protein. Various methods of associating the whey protein with the lipophilic bioactive compound are provided. The primary composition may be administered to the subject by various means, including oral administration by adding the composition to a foodstuff, a food supplement or a pharmaceutical preparation.

Further, a method of providing increased photostability and oxidation resistance to a lipophilic bioactive compound is provided. Such method comprises associating the lipophilic bioactive compound with a whey protein to form a primary composition, wherein the whey protein is present in an amount sufficient to increase the photostability and oxidation resistance of the lipophilic bioactive compound compared to lipophilic compositions that do not include whey protein.

DETAILED DESCRIPTION OF THE INVENTION

The present invention relates to a primary composition comprising a LBC and a whey protein. By providing a primary composition in which a LBC is provided in an unencapsulated form and is associated with a whey protein such that the bioavailability of the LBC is increased, the present invention now makes available to the consumer an improved composition obtained from natural products. Through the novel feature of associating the LBC with a whey protein to form a mixture or matrix, the present invention provides protection and enhancement of the LBC.

As used herein, the term "bioactive compound" is understood to mean a compound having a beneficial effect on the human or animal metabolism. The LBC is obtained, extracted, enriched or purified starting from a plant, microorganism, yeast or product of animal origin. The term "obtained" is understood to mean that the bioactive product is directly available commercially. The term "extracted" is understood to mean that the bioactive principle has been extracted. The term "enriched" is understood to mean that the non-bioactive compounds have been separated as much as possible. The term "purified" is understood to mean that only the bioactive compound is recovered.

In the case of a bioactive compound originating from a plant, the plant is chosen from the group consisting of tomatoes (i.e., whole tomato, tomato extract, tomato flesh, tomato puree, tomato skin, with or without the seeds), soya, green tea, green coffee beans, spices such as ginger or others, grapes, cocoa and cereals. The microorganism can be any type of bacterium which produces a LBC. For example, a probiotic microorganism, in particular a lactic acid bacterium, can be envisaged as microorganism. The yeast can be any yeast which produces a LBC, for example a Saccharomyces. The product of animal origin is chosen from the group consisting of a liver extract and a milk fraction. The term "milk fraction" is understood to mean any part of the milk.

In the primary composition according to the invention, the LBC may be chosen from the group consisting of carotenoids, polyphenols, lipophilic vitamins, flavonoids, isoflavones, curcuminoids, ceramides, proanthocyanidins, terpenoids, sterols, phytosterols, sterol esters, tocotrienols, squalene and retinoids, alone or as a mixture. Carotenoids are present in particular in tomatoes, carrots, yellow peaches, apricots and oranges. Lycopene is a carotenoid which is particularly favored in the present composition. Polyphenols are present in particular in green tea, coffee, cocoa or red wine. Lipophilic vitamins are present in particular in numerous vegetables. Flavonoids and isoflavones are present in particular in soya, tea, onions or wine. Curcuminoids are present in particular in ginger. Ceramides are glycolipids present in particular in yeast derivatives and derivatives of animal origin. Proanthocyanidins are flavonoids present in particular in grapes. Terpenoids are present in spices. Sterols, phytosterols and sterols esters are present in particular in vegetable oils, seeds, nuts and vegetables. Tocotrienols are present in particular in rice bran, barley, wheat, palm oil, rye and oats. Squalene is present in particular in fish liver, olive oil, wheat germ oil or rice bran oil. Finally, retinoids are present in particular in liver, egg yolk and dairy products.

In a preferred embodiment of the primary composition according to the invention, the LBC is obtained from tomatoes, for example tomato puree or a tomato extract. The presence of lycopene in tomatoes is advantageous for the present invention. The bioactive compound can also be a soybean extract. It is also possible to have a mixture of tomato extract and of soybean extract. These extracts are obtained by conventional methods, with the preferred tomato extract being a lipidic extract obtained by use of a solvent such as ethyl acetate, and the soybean extract being obtained from the ethanol/hot water extraction of soy which has been initially defatted by treatment by hexane.

The composition according to the invention can be provided in the form of a powder, liquid or gel. Where the powder form is chosen, the composition may be in the form of a highly water-dispersible composition, as the powder is dispersible in water at ambient temperature.

The present invention provides a composition comprising a LBC which has a better bioavailability than when the compound is provided alone. Such enhanced bioavailability of the LBC is achieved by associating the LBC with a whey protein in a mixture/matrix, i.e., in an unencapsulated form. It has been surprisingly discovered that the bioavailability of a LBC can be enhanced by associating the LBC with whey protein such that the LBC and the whey protein are provided in a form of a mixture or a matrix. Thus, the invention advantageously provides a method for increasing bioavailability of a lipophilic bioactive compound to a subject upon administration by: associating a whey protein with the lipophilic bioactive compound in a mixture or matrix to form a primary composition, wherein the whey protein is present in an amount sufficient to increase the bioavailability of the lipophilic bioactive compound to the subject upon administration, and administering the primary composition to the subject wherein increased amounts of the lipophilic bioactive compound are released compared to lipophilic compositions that do not include whey protein.

Further, by providing the LBC in an unencapsulated form and in mixture with whey protein, the present invention also seeks to protect and preserve the activity of the LBC. In particular, it has been found that the compound's resistance to decomposition by light and oxygen is significantly increased by associating the LBC with whey protein as provided in the present invention. Thus, the present invention provides a method for increased photostability and oxidation resistance to a LBC by associating the LBC with a whey protein in a mixture or matrix.

In the compositions according to the invention, the preferred additive for increasing bioactivity of the compound is whey protein, for example in the form of whey protein isolate. The term "whey protein" is understood to mean a product comprising at least 80% of whey proteins. "Whey protein" as used herein indicates a product of dairy origin, which comes from the watery part of milk that separates from the curd, as in the process of making cheese, left over after butterfat, casein and albumin are removed.

The primary composition according to the invention can additionally comprise vitamin E and vitamin C. Vitamin E (tocopherol) can be of exogenous or endogenous origin. If desired, vitamin C in any conventional form may be added to the composition.

The composition additionally comprises one or more of emulsifiers, stabilizers and other additives. Use is made of emulsifiers compatible in the food field, such as phospholipids, for example lecithin, polyoxyethylene sorbitan mono- or tristearate, monolaurate, monopalmitate, mono- or trioleate, a mono-or diglyceride. Use may also be made of any type of stabilizer that is known in the food business, in cosmetics or in pharmaceuticals. Use is made, as additives, of flavorings, colorants and any other additive known in the food business, in cosmetics or in pharmaceuticals. These emulsifiers, stabilizers and additives are added according to the final use of the primary composition.

In the primary composition, the LBC is preferably present in an amount of about 0.05 to 50% by weight of the composition and the whey protein is present in an amount of about 5 to 90% of the composition. Also, the whey protein and LBC may be present in a weight ratio of at least about 1:1 to 500:1, preferably from about 1.5:1 to 250:1 and more preferably about 2:1 to 20:1.

In a preferred embodiment of the invention, the primary composition comprises tomato oleoresin, soybean extract and whey protein. The term "tomato oleoresin" is understood to mean, in the present description, a lipid extract of the tomato plant, including carotenoids, such as lycopene, triglycerides, phospholipids, tocopherol and other less significant compounds. The term "soybean extract" is understood to mean a soybean extract comprising a high content of isoflavone. It is also possible to envisage other carotenoid-comprising plants, in particular melons, guavas, grapefruit, apricots, rosehips, carrots, peaches and oranges.

The present invention additionally relates to an oral composition comprising the primary composition described above in a foodstuff, in a food supplement, in a cosmetic preparation or in a pharmaceutical preparation.

This orally ingestible composition makes it possible to enhance the bioavailability of the LBC in the body and to slow down the ageing of the skin. Mention may be made, as foodstuff supplemented by the above primary composition, of yogurts, liquid drinks, chocolate, ice creams, cereals, chocolate powders, coffee, culinary products, such as mayonnaise, tomato puree or salad dressings, infant nutrition products, enteral nutrition products or pet foods. In this case, the powder is dissolved in the above-mentioned foods or drinks so as to have a daily intake of between about 0.001 and 50 mg of LBC, for example such as lycopene. A daily intake of the order of about 5 to 20 mg per day is preferably envisaged.

It is also possible to envisage, according to the invention, a food supplement in the form of sugar-coated tablets, pills, gelatin capsules, a syrup, a gel, a cream or lozenges with a dose of about 0.001 to 100% of the primary composition, which can then be taken directly with water or by any other known means. This supplement may also include a sweetener, a stabilizer, an additive, a flavoring or a colorant.

The oral composition can also be a cosmetic preparation comprising the primary composition and a compound active with respect to the skin known to a person skilled in the art.

The oral composition can also be a pharmaceutical preparation comprising the primary composition and a pharmaceutical compound, for example a compound in topical application or which can be orally ingested.

The invention also relates to a cosmetic composition comprising the primary composition described above. In this case, the content of primary composition is between $10^{-10}$ and 10%. The cosmetic composition preferably comprises between $10^{-8}$ and 5% of LBC.

This composition which can be used topically additionally comprises a fat or an oil which can be used in cosmetics, for example those mentioned in the CTFA work, Cosmetic Ingredients Handbook, Washington. It is also possible to add other cosmetically active ingredients. The composition additionally comprises a structuring agent and an emulsifier.

Other excipients, colorants, fragrances or opacifiers can also be added to the composition. The present invention additionally relates to the use of the oral composition or of the cosmetic composition described above for protecting the tissues of the skin against ageing, in particular for inhibiting damage to the skin and/or mucous membranes by inhibiting collagenases and enhancing the synthesis of collagen.

The present invention additionally relates to the process for the preparation of the primary composition described above, in which the whey protein is associated with the LBC in a non-encapsulated form.

In one embodiment of the process according to the invention,
the whey protein is dissolved in water;
the LBC is dissolved in a solvent;
the two solutions are mixed;
the solvent is evaporated; and
a dispersion is obtained.

In a first alternative form of the process according to the invention, a dispersion is obtained. In a second alternative form, the dispersion is heat-treated to produce a gel. And, in a third alternative form, the dispersion is dried by spraying or by lyophilization to produce a powder. The composition according to the invention may be directly usable as is or as a mixture, as will be explained below.

The whey protein is dissolved in water at a temperature in the region of or slightly greater than ambient temperature. An oleoresin which comprises between I and 40% of lycopene is used. The amounts are given as weight/weight. When the oleoresin is dissolved in the solvent, the ratio of the said oleoresin to the solvent is of the order of 1:1 to 1:900 by weight.

The solvent is any type of solvent compatible with the food business, cosmetics or pharmaceuticals. The solvent is preferably acetone, ethanol or isopropanol. When the aqueous phase is mixed with the solvent, a solvent/water ratio by volume of the order of 60/40 is chosen.

After mixing the two phases, the mixture is left to stand for 30 to 60 mm at a temperature slightly higher than ambient temperature, for example of the order of 30° C., and the first operation is to drive off the solvent under a moderate vacuum. The term "moderate vacuum" is understood to mean a vacuum of between 200 and 300 mbar. If a powder is desired, the water is removed, either under vacuum or by spraying or by lyophilization. The term "vacuum" is understood to mean a vacuum of between 40 and 50 mbar. If a gel is desired, the emulsion is heated or any other technique known to a person skilled in the art for preparing the said gel is employed.

In another embodiment of the process according to the invention,
the LBC is mixed with a solvent;
the composition obtained is mixed with the whey protein powder; and
the solvent is evaporated to produce a powder composition.
The solvent used is the same as that mentioned above.

In yet another embodiment, the LBC, either in the oleoresin form or in the powder form or in any other dry form (for example, the oleoresin is absorbed on a support), is mixed directly with the whey powder (optionally comprising a soybean extract) to produce the primary composition according to the invention.

EXAMPLES

The continuation of the description is now made with reference to the examples which illustrate preferred embodiments of the invention.

Example 1

Preparation of the Composition in the Powder Form 13.3 kg of whey protein isolate are dissolved in 330 l of demineralized water and the mixture is stirred for 6 hours at 25-30° C. Separately, 550 g of oleoresin from Lycored, comprising 6% of lycopene, are mixed in 438 l of acetone and the mixture is stirred.

The two solutions are subsequently mixed for 60 mm at 30° C. The final mixture is moderately heated and the acetone is driven off at a moderate pressure. Finally, water is partially driven off at a pressure of 40-50 mbar. An aqueous solution of 200 kg of whey protein isolate and of oleoresin is obtained.

This solution is subsequently spray dried.

Starting from this powder, tests were carried out with thirty six individuals. After a three-week deprivation period of dietary lycopene intake, the subjects were divided into three groups: (a) group that ingested lycopene-whey protein formulation prepared above; (b) group that ingested tomato paste as positive control; and (c) group that ingested a placebo of whey proteins. Over eight weeks, the subjects in group (a) were daily given the powder comprising 25 mg of lycopene and other carotenoids present in the oleoresin and 12.5 g of whey proteins. The powder was taken by dissolving it in apple juice.

In comparison to the positive control group (b) which ingested tomato paste comprising the same amount of lycopene, the bioavailability of the lycopene from the lycopene-whey protein was similar to the bioavailability of lycopene from the tomato paste, as determined by the quantitative analysis of the lycopene level in the blood plasma. The level of lycopene in blood plasma was determined by extracting plasma and buccal mucosa samples, from which lycopene was isolated from other carotenoids and tocopherols by HPLC using a C18 RP column. The lycopene level was then further quantified by UV/V is detector. Table 1 compares the plasma lycopene levels of the three test groups and summarizes the results of the study.

TABLE 1

| | Plasma phytofluence | | | | Plasma lycopene | | | |
|---|---|---|---|---|---|---|---|---|
| | Supplement mg | Week 0 µg | Week 8 µg | Change µg | Supplement mg | Week 0 µg | Week 8 µg | Change µg |
| (a) Lctolycopen | 2 | 0.2 ± 0 | 0.4 ± 0.1 | 0.2 ± 0.1 | 25 | 0.4 ± 0.1 | 1.0 ± 0.1 | 0.6 ± 0.1 |
| (b) Tomato paste | 2 | 0.2 ± 0 | 0.5 ± 0.1 | 0.3 ± 0.1 | 25 | 0.3 ± 0 | 0.8 ± 0.1 | 0.5 ± 0.1 |
| (c) Placebo | 0 | 0.2 ± 0.2 | 0.2 ± 0 | 0 ± 0 | 0 | 0.3 ± 0 | 0.3 ± 0.1 | 0.1 ± 0.1 |

Note:
Phytofluence is the precursor of lycopene.

It should be remembered that tomato paste is regarded by a person skilled in the art as the product having the best bioavailability of lycopene. Thus, the study shows that the bioavailability of lycopene is significantly increased when associated with whey protein as in the present composition, as compared to when it is provided in fresh tomatoes, tomato extracts or in such other products where the lycopene is not associated with whey protein.

Example 2

Preparation of Sugar-Coated Tablets

A dispersion of 550 g of oleoresin of Example 1 with an emulsifier in ethanol is prepared. This dispersion is mixed with 1100 g of whey protein and 1100 g of soybean extract (comprising 40% of isoflavone). The solvent is driven off to produce a powder.

The powder thus obtained is mixed with ascorbic acid and other additives, such as one or more sweeteners, thickeners and food additives, making possible preparation in the form of sugar-coated tablets. The mixture obtained is subsequently sugar-coated.

Sugar-coated tablets of the order of 700 mg, comprising 33 mg of lycopene, 70 mg of soybean extract, 70 mg of whey protein, 40 mg of ascorbic acid, the remainder being sweeteners, thickeners and food additives, to arrive at 700 mg, are thus prepared.

Example 3

Cosmetic Composition

A milk for the face is prepared comprising 7% of liquid petrolatum, 2% of powder according to Example 1, 3% of glyceryl monostearate, polyethylene glycol stearate, 0.4% of carboxyvinyl polymer, 0.7% of stearyl alcohol, 3% of soybean proteins, 0.4% of NaOH and a preservative, and the remainder to 100% being water.

Example 4

Cosmetic Composition

A gel for the face is prepared comprising 10% of glycerol, 2% of powder according to Example 1, 1% of disodium cocoamphodiacetate and a preservative, and the remainder to 100% being water.

Example 5

Study of the Stability of Lycopene

It is known that light and oxygen cause lycopene to decompose. An aqueous-phase analysis of the stability of lycopene alone and of lycopene in combination with the whey protein according to the invention was carried out. After one day in the aqueous phase for lycopene alone, only 40% of the lycopene remains, whereas, with the whey, virtually 90% of it, remains. After two days, 60% of it remains with the whey, whereas the lycopene is virtually completely decomposed if it is alone.

A protective effect on the lycopene by the whey protein therefore clearly exists.

What is claimed is:

1. A primary composition consisting essentially of a mixture or matrix of i) at least one lipophilic bioactive compound that is lycopene, ii) a dairy-based whey protein, and iii) a component selected from the group consisting of a vitamin, an emulsifier, a stabilizer, and combinations thereof, the whey protein present in an amount sufficient to increase the bioavailability of the lipophilic bioactive compound, wherein increased amounts of the lipophilic bioactive compound are released upon administration of the primary composition as compared to lipophilic compositions that do not include whey protein, wherein the whey protein is associated with the lipophilic bioactive compound in a non-encapsulated form and wherein the primary composition is in the form of a powder.

2. The primary composition according to claim 1, wherein the lipophilic bioactive compound is obtained, extracted, enriched or purified from tomatoes.

3. The primary composition according to claim 1, wherein the primary composition consists of the at least one lipophilic bioactive compound, the dairy-based whey protein, and the component selected from the group consisting of a vitamin, an emulsifier, a stabilizer, and combinations thereof.

4. An oral composition comprising the primary composition according to claim 1 in a foodstuff, in a food supplement, or in a pharmaceutical preparation.

5. The oral composition according to claim 4, wherein the foodstuff is a yogurt, a liquid drink, a chocolate containing product, an ice cream, cereal, coffee or animal food.

6. The oral composition according to claim 4, wherein the food supplement further comprises at least one of a sweetener, a stabilizer, a flavoring or a colorant.

7. The oral composition according to claim 4, wherein the pharmaceutical preparation is provided in the form of sugar-coated tablets, pills, gelatin capsules, a syrup, a gel or a cream.

8. The oral composition according to claim 4, wherein the content of the primary composition is between about 0.001 and 100%.

9. The oral composition according to claim 8, wherein the content of the primary composition is between about 10 and 50%.

10. The primary composition according to claim 1, wherein the lipophilic bioactive compound is present in an amount of about 0.05 to 50% by weight of the composition and the whey protein is present in an amount of about 5 to 90% by weight of the composition and wherein the whey protein and the lipophilic bioactive compound are present in a weight ratio of about 1.5:1 to 250:1.

11. A cosmetic composition comprising the primary composition of claim 1 and a cosmetic ingredient selected from the group consisting of petrolatum, glyceryl monostearate, polyethylene glycol stearate, carboxyvinyl polymer, stearyl alcohol, disodium cocoamphodiacetate and combinations thereof.

12. The cosmetic composition according to claim 11, wherein the content of primary composition is between about $10^{-10}$% and 10%.

13. An oral primary powder consisting essentially of a mixture or matrix of i) at least one lipophilic bioactive compound and ii) a dairy-based whey protein, the whey protein present in an amount sufficient to increase the bioavailability of the lipophilic bioactive compound, wherein increased amounts of the lipophilic bioactive compound are released upon administration of the primary composition as compared to lipophilic compositions that do not include whey protein and wherein the whey protein is associated with the lipophilic bioactive compound in a non-encapsulated form, the powder consisting of the at least one lipophilic bioactive compound and the dairy-based whey protein.

* * * * *